United States Patent
Islam et al.

(10) Patent No.: US 6,740,505 B1
(45) Date of Patent: May 25, 2004

(54) PRODUCTION OF PROTEINS

(75) Inventors: Seema Islam, New York, NY (US); Nigel Alan Sharp, Stevenage (GB)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/868,666

(22) PCT Filed: Dec. 21, 1999

(86) PCT No.: PCT/EP99/10157

§ 371 (c)(1), (2), (4) Date: Nov. 28, 2001

(87) PCT Pub. No.: WO00/39282

PCT Pub. Date: Jul. 6, 2000

(30) Foreign Application Priority Data

Dec. 23, 1998 (GB) .............................. 9828624

(51) Int. Cl.$^7$ ................................ C12P 21/00
(52) U.S. Cl. .................... 435/69.1; 435/69.2; 435/69.4; 435/69.5; 435/69.6; 435/70.1
(58) Field of Search ............... 435/69.1, 69.2, 435/69.4, 69.5, 69.6, 70.1

(56) References Cited

U.S. PATENT DOCUMENTS

| | | | |
|---|---|---|---|
| 5,378,612 A | 1/1995 | Nakashima et al. ........ | 435/69.6 |
| 5,681,718 A * | 10/1997 | Field ......................... | 435/69.2 |
| 5,705,364 A * | 1/1998 | Etcheverry et al. ........ | 435/70.3 |
| 6,117,652 A * | 9/2000 | Field ......................... | 435/69.2 |
| 6,228,618 B1 * | 5/2001 | Field ......................... | 435/69.2 |
| 6,413,746 B1 * | 7/2002 | Field ......................... | 435/70.2 |
| 6,506,598 B1 * | 1/2003 | Andersen et al. .......... | 435/359 |
| 6,610,516 B1 * | 8/2003 | Andersen et al. .......... | 435/70.1 |
| 6,660,501 B2 * | 12/2003 | Field ......................... | 435/70.2 |

FOREIGN PATENT DOCUMENTS

| EP | 0 239 292 A | 9/1987 |
|---|---|---|
| WO | WO 89 06686 A | 7/1989 |
| WO | WO 96 39488 A | 12/1996 |

OTHER PUBLICATIONS

Chotigeat W. et al., *Role of Environmental Conditions on the Expression Levels, Glycoform Pattern and Levels of Sialyltransferase for HFSH Produced by Recombinant CHO Cells. Cytotechnology*, NL. Kluwer Academic Publishers, Dordrecht, 15(1/03):217–221 XP000602299 (1994).

D.P. Palermo et al., *Production of analytical quantities of recombinant proteins in Chinese hamster overy cells using sodium butyrate to elevate gene expression. J. Biotechnology*, 19(1):35–48 XP002135791 (1991).

Goldstein S. et al., *Enhanced Transfection Efficiency and Improved Cell Survival After Electroporation of G2/M–Synchronized Cells and Treatment with Sodium Butyrate, Nucleic Acids Research*, GB, Oxford University Press. Surrey, 17(10):3959–3971 XP002054817 (1989).

Gorman C.M. et al., *Expression of Recombinant Plasmids in Mammalian Cells is Enhanced by Sodium Butyrate. Nucleic Acids Research*, GB, Oxford University Press, Surrey, 11(2):7631–7648 XP002054816 (1983).

Bebbington et al., "High–level expression of a recombinant antibody from myeloma cells using a glutamine synthetase gene as an amplifiable selectable marker," *Nature Biotechnology* 10:169–175 (Feb. 1992).

de Haan et al., "Effects of sodium butyrate on the synthesis and methylation of DNA in normal cells and their transformed counterparts," *Cancer Research* 46(2):713–716 (1986).

* cited by examiner

*Primary Examiner*—David Saunders
(74) *Attorney, Agent, or Firm*—Virqinia C. Bennett

(57) ABSTRACT

A process for the production of a protein by cell culture, said process comprising culturing eukaryotic cells which constitutively produce said protein in a medium which comprises an alkanoic acid and/or salt thereof at a maintained concentration of less than 0.1 mM.

26 Claims, 2 Drawing Sheets

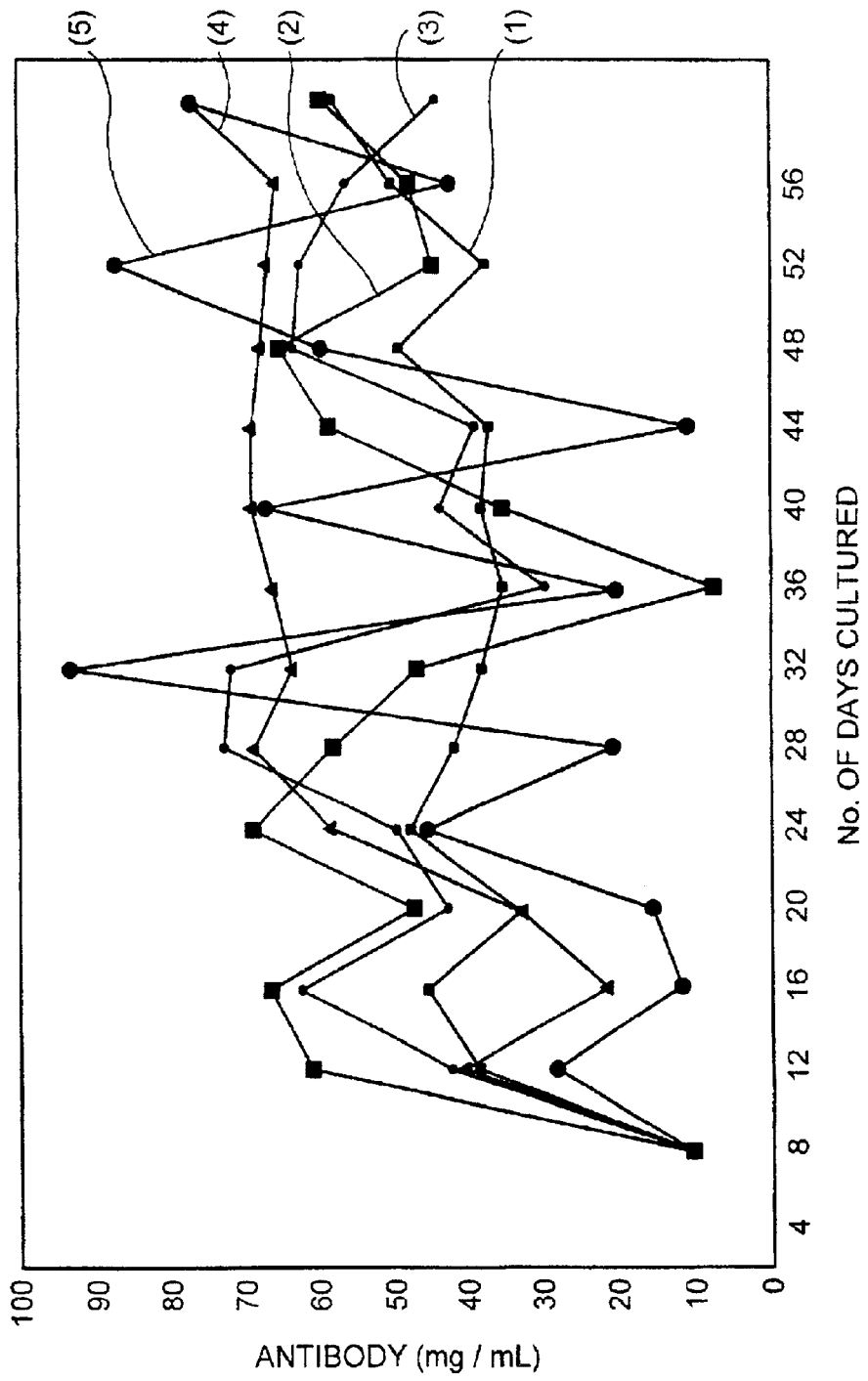

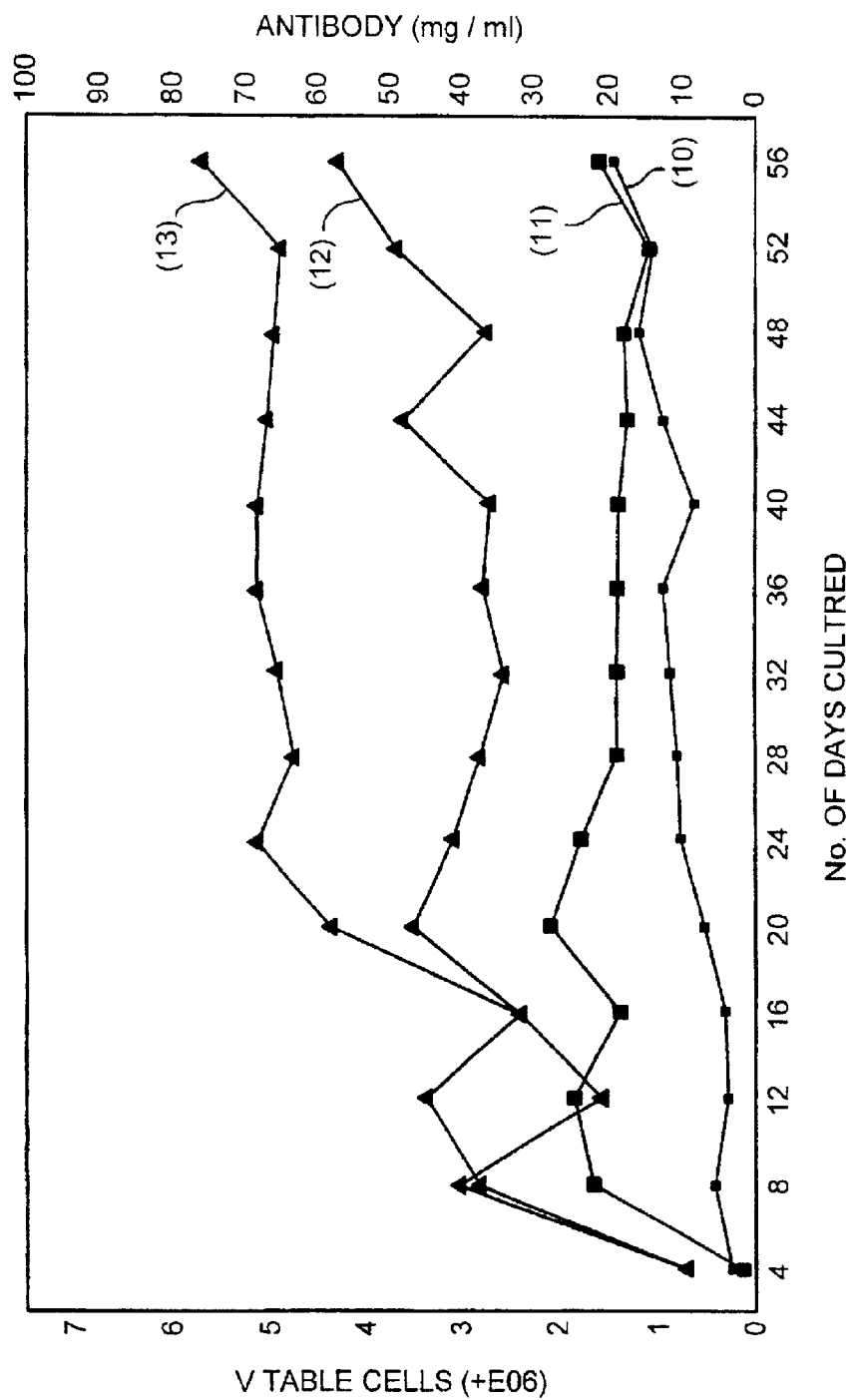

PRODUCTION OF PROTEINS

This application is filed pursuant to 35 U.S.C. §371 as a United States National Phase Application of International Application No. PCT/EP99/10157 filed Dec. 21, 1999, which claims priority from Great Britain Application No. 9828624.8 filed Dec. 23, 1998.

The present invention concerns the production of proteins by cell culture techniques and in particular concerns new and improved processes for the production of proteins useful in therapeutic and diagnostic applications.

The commercial production of proteins by cell culture particularly for use in medical applications remains a costly exercise principally due to the relatively low levels of proteins (particularly so-called "rare proteins") produced by many cell types. One approach to addressing this problem is the use of agents to induce cells to produce higher than normal amounts of the desired protein. An example of such an agent is butyric acid or, more typically, a salt thereof such as sodium butyrate, which is believed to modify gene expression at a molecular level through its effect on the methylation state of DNA, which in turn affects transcriptional gene activation. The inducing agent supplements the culture media during the culturing process and is typically following a period of cell culturing. During the process the culture media including the inducing agent may be changed by either a continuous process in which new media is continually added as old medium is removed or in a batch type process in which some of the medium is removed from the cells and replaced.

In EP 0 239 292 B1, NB1/19 cells were incubated with a variety of sodium butyrate concentrations ranging from 0.1 mM to 1.0 mM for a period of only approximately 8 days. In WO 89/06686, a process of enhancing protein production by cultured eukaryotic cells through the addition of butyric acid or salt thereof in concentrations of 0.1 mM to 10.0 mM is suggested. In this disclosure, cells are first grown to confluence before the addition of the acid or salt. This is generally in line with accepted thinking that butyric acid, whilst effective in promoting protein production, also has a potentially deleterious effect on the viability of cells, making it prudent to bring cells to confluence or to a relatively high cell population, before exposing them to the butyric acid.

In U.S. Pat. No. 5,705,364, the use of an alkanoic acid or salt thereof at concentrations of between 0.1 mM and 20 mM in optional conjunction with osmotic control to specifically increase silac acid content of glycoproteins is discussed. In Nucleic Acids Res., 1983, 11, no.21 the effects of sodium butyrate on DNA-mediated gene transfer is investigated at concentrations ranging from 2 to 10 mM. In Can.Res, Vol.46, February 1986, 713–716, an investigation into the effects of sodium butyrate on the synthesis and methylation of DNA in normal cells and their transformed counterparts is disclosed. In this investigation, concentrations ranging from 5 to 100 mM are used. In U.S. Pat. No. 5,378,612, a culture medium for culturing transformed cells is disclosed. The culture media may contain butyric acid at an exemplified concentration of 1 mM.

The present inventors have found, contrary to conventional expectations, that the use and maintenance of unusually low concentrations of an alkanoic acid in culture media comprising culturing cells, leads to enhanced protein production without, over an extended period of time, significantly affecting cell viability. Furthermore, the low alkanoic acid concentration permits the presence of alkanoic acid in the culturing media at an earlier stage in the culturing process than hitherto described.

In accordance with the present invention, we provide a process for the production of a protein by cell culture which comprises the step of culturing eukaryotic cells which constitutively produce e.g. secrete, said protein in a culture media which media comprises an alkanoic acid and/or salt thereof at a maintained concentration of less than 0.1 mM.

In accordance with the present invention, we provide a process for the production of a protein by cell culture which comprises the steps of (a) culturing eukaryotic cells which constitutively produce e.g. secrete said protein in a culture media which media comprises an alkanoic acid and/or salt thereof at a concentration of less than 0.1 mM (b) subculturing the cell culture (c) supplementing the subculture media with additional alkanoic acid and/or salt thereof to maintain the concentration therein during the culturing process at less than 0.1 mM.

Novel proteins obtained by the process of the present invention as hereinbefore described also forms an aspect of the present invention.

It will be understood by those skilled in the art that the terms "maintained concentration" and "to maintain the concentration" does not necessarily imply that the concentration in the culturing media must be kept constant since a certain degree of variation in concentration is permissible whilst still achieving the same or similar results. Of course, Zero mM is excluded from the term "less than 0.1 mM".

In accordance with the present invention we provide a process for the production of a protein by cell culture which comprises the steps of (a) culturing eukaryotic cells which constitutively produce e.g. secrete said protein in a culture media which comprises an alkanoic acid and/or salt thereof at a specified concentration which concentration is less than 0.1 mM.

Eukaryotic cells useful in the practice of the present invention may be e.g. yeast or animal and be anchorage dependent or independent. Preferably, the cells are mammalian e.g. rat, mouse and hamster. Cells of the present invention may be immortalised cells. Immortalised cells may be transformed or transfected with exogenous DNA e.g. via a plasmid, coding for the desired protein according to techniques standard and well known to those skilled in the art. Cells for use in the present invention include hybridoma cells e.g. hybrid cells produced by fusion of antibody producing cells with myeloma cells. The process of the present invention maybe used in the culturing of hybridoma cells for the production of immunoglobulins e.g. antibodies.

Cells useful in the present invention include NS0 cells (non-immunoglobulin secreting mouse myeloma B cells), and CHO cells (Chinese hamster ovaries). Preferably, cells of the present invention are derived from stable cell lines, the production of which is well known to those skilled in the art. For example, stable cell line expression may be produced using a glutaminine synthetase gene amplification system (such as commercially available from Celltech). Briefly, linearized expression vectors containing cDNA encoding e.g. hamster glutamine synthetase, under the control of an Early promoter such as SV40 and splicing and polyadenylation signals and cDNA of the desired protein, e.g. antibody heavy and light chains are introduced into mammalian cells by electroporation. Transfected cells are then selected for the ability to grow in, for example, a glutamine free medium. See Bebbington et al, 1992, Biotechnology 10, 169–175 to which the reader is specifically referred.

Proteins which maybe produced by the present invention include therapeutically and/or diagnostically useful eukaryotic proteins which may be naturally occuring or artificial (e.g. fusion proteins). Examples of proteins whose production may benefit from the present invention include hormones, for example growth hormone e.g. human growth hormone, enzymes, enzyme inhibitors or lymphokines. The process of the present invention is particularly useful in the production of immunoglobulins, e.g. naturally occurring and artificial (chimeric and humanised) antibodies or analogues or fragments thereof Suitable fragments thereof include Fab, Fv fragments and single chain antibodies. Antibodies maybe polyclonal or more preferably monoclonal from any suitable class or subclass. It is preferred that the antibody is a IgG, particularly $IgG_1$ antibody or fragment derived therefrom. Preferably such proteins are suitable for use in the therapeutic (including prophylactic) or diagnostic treatment of human diseases, e.g. pro-inflammatory disorders such as rheumatoid arthritis, osteoarthritis, or other disorders. Thus in the case of antibodies, the antibody may be produced in a humanised form.

The alkanoic acid or salt thereof of the present invention, is preferably a straight chain $C_{2-10}$, especially $C_{3-6}$ and in particular is butyric acid or metal salt thereof, e.g. sodium butyrate. Systems and processes for the detection of alkanoic acids and salts, e.g. chromatography, will be readily apparent to those skilled in the art. Preferably, the acid and/or salt thereof is kept at a concentration in the cell culture media, which whilst less than 0.1 mM, is greater than 0.025 mM, preferably greater than 0.05 mM.

In a preferred embodiment, particularly for NS0 cells, the acid and/or salt thereof is present within the cell culture media at a concentration of about 0.075 mM. These concentrations provide useful protein production with, over an extended period, minimal adverse effect on cell viability. Furthermore, the production of protein by cells exposed to these concentrations appears less erratic over time than at higher concentrations, for example 0.1 mM. This is beneficial in providing greater consistency during any harvesting of protein that may take place during the culturing process. Furthermore a degree of control is provided over the process which, it will be appreciated, is desirable during commerical manufacturing processes.

It will be apparent to those skilled in the art that routine experimentation by e.g. simple titre experiments, may be employed to empirically determine the concentration or range of concentrations of acid and/or salt thereof in which, for a given cell type, enhanced protein production is evident with minimal adverse affect on cell viability particularly over an extended time period as measured by e.g. a simple viability count.

In accordance with the present invention we provide a process for the production of a protein in cell culture which comprises the steps of culturing eukaryotic cells which constitutively produce e.g. secrete said protein in a culture media which media comprises an alkanoic acid and/or salt thereof at a concentration, particularly less than 0.1 mM, which concentration being sufficient to promote e.g. increase, protein production in the cells with minimal, preferably no, adverse affect on cell viability particularly when the cells are cultured for an extended period, e.g. greater than 10 days, more preferably greater than 30 days, even more preferably, greater than 50 days.

It is preferred that the concentration of the acid and/or salt within the culture media is maintained at approximately the same concentration during the culturing process (the specified concentration), preferably during a major proportion of the culturing process, more preferably, the entire time in which the acid and/or salt is present within the culture media. Where variation in concentration does occur, suitably such variation is within +20 mM, aptly, ±10 mM, of the specified concentration.

The cell culture media of the present invention maybe comprise serum (e.g. animal serum such as fetal calf serum) or be serum free and may further comprise the usual components found in standard cell culture media. Those skilled in the art will appreciate that in circumstances where e.g. a glutamine dependency assay is employed, the culture media should comprise little, preferably, no, glutamine. The acid and/or salt is preferably admixed with the culture media prior to, at the start or shortly after commencement of the culturing process.

It is particularly preferred that the acid and/or salt thereof supplements the media following a short period from commencement in which the cells are cultured in the absence of acid and/or salt thereof to facilitate establishment of a protein-producing (i.e. stable) cell population. It is preferred that the cells are cultured for the minimum period of time necessary to establish the protein producing population prior to the addition of acid and/or salt. The short period may be determined empirically for a given cell line, for example, for NS0-GS cell line, the short period is about 4 days.

Maintenance of the concentration of the acid and/or salt thereof may be achieved by supplementing the media with additional acid and/or salt thereof by a fed-batch type process (in which cells and the culture medium are supplied to a culture vessel initially and additional culture nutrients are fed continuously, or in discrete increments, to the culture during the culturing process) or alternatively through a continuous (i.e. perfusion) process in which new media is continually added as old medium is removed.

In preferred forms, a portion of the culture is subcultured by e.g. a draw-fill process wherein a portion of the culture is removed during the culturing process, the culture media adjusted and culturing of the remaining cells continued. The subculture is supplemented with additional acid and/or salt to adjust and therefore maintain the concentration therein at less than 0.1 mM. The entire culturing process preferably takes place over an extended time course, i.e. greater than 10 days, preferably, greater than 40 days.

Preferably, the acid and/or salt is continuously present within the culture media during at least a portion of the culturing process. In particular, it is preferred that the acid and/or salt thereof is continuously present in the culture media over a major proportion of the culturing process, most preferably, the entire process.

Examples of culturing systems that may be employed in the present invention include fluidized bed bioreactors, hollow fiber bioreactors, roller bottle culture or stirred tank bioreactors. Generally, the culturing of cells comprises submerging the cells (at a density of e.g. $0.2 \times 10^5$/ml) in the culture media contained within a suitable vessel. The media comprising cells and the acid and/or salt is then exposed to appropriate temperature (e.g. 36° C.), pressure, pH, humidity and other conditions, over a period of time.

The process of the present invention may be used in conjunction with other techniques for increasing protein production in culturing cells, e.g. osmotic stressing of the culturing cells.

The desired protein may be isolated or recovered from the cell culture by conventional separation techniques. This may take place during or following termination of the culturing process. Such conventional techniques include centrifugation to remove particulate cell debris wherein the supernatant collected after the centrifugation step is treated by e.g. ultrafiltration, fractionation on immunoaffinity or ion-exchange columns or other chromatographic techniques and subjected to further purification techniques to purify, if desired, to homogeneity.

Proteins produced by the present invention may be used in the manufacture of pharmaceutical compositions which comprise an effective amount of the protein together with other constituents such as a pharmaceuticallly acceptable carrier as known and called for by accepted pharmaceutical practice. Such other constituents may include other therapeutic agents. Determination of the effective amount may be ascertained by routine experimentation and observation as known to those skilled in the art.

Suitably, such pharmaceutical compositions are made available in unit dosage form. Pharmaceutical compositions maybe in any form appropriate for the route of administration which, it will be appreciated, is dictated in part by the prevailing circumstances, e.g. condition to be treated. Thus, pharmaceutical compositions may be in the form of capsules, cachets, tablets, powders or granules, suspensions in a sterile aqueous or non-aqueous liquid, onitment, paste or paint. Pharmaceutcal compositions may be used in conjunction, e.g. as part of a treatment regimen, with other therapeutic and/or diagnostic agents. It is particularly envisaged that proteins of the present invention are used in the therapeutic and/or diagnostic treatment of mammals including humans.

The present invention will now be illustrated, by way of example only, and with reference to the following figures, in which:

FIG. 1 illustrates the comparison of antibody production in NS0 cell culture when cultured in media supplemented with five concentrations of sodium butyrate (0~0.1 mM) over a period of 56 days. The following reference numerals denote concentration used:

(1): 0 mM sodium butyrate
(2): 0.025 mM sodium butyrate
(3): 0.05 mM sodium butyrate
(4): 0.075 mM sodium butyrate
(5): 0.1 mM sodium butyrate.

FIG. 2 illustrates enhancement of antibody production by NS0 cells cultured in 0.075 mM sodium butyrate in repeated batch culture. The following reference numerals denote:

(10): viability of cells without butyrate supplementation (control)
(11) viability of cells supplemented with sodium butyrate (0.075 mM)
(12) antibody titre of control cells (10)
(13) antibody titre of cells (11)

Example 1

Five Erlenmeyer flasks were inoculated with recombinant murine NS0 cells transfected with a $IgG_1$ humanised anti-CD23 antibody (produced according to the method of Bebbington et al, as supra) in a cholesterol containing protein free/glutamine free medium at $0.2 \times 10^6$ cells/ml. Sodium butyrate (0.5M) in PBS was added to the flasks at the following concentrations: 0 mM; 0.025 mM; 0.05 mM; 0.075 mM and 0.10 mM and were incubated at 36°0 C. and 100 rpm in a shake incubator for 4 days. Subsequently, the flasks were subcultured every four days to a start count of $0.2 \times 10^5$ cells/ml, maintaining sodium butyrate concentrations as above in each flask. The flasks were sampled and assayed before each subculture. The culture was continued in this 'draw-fill'/'repeated batch' manner for 56 days, maintaining sodium butyrate concentrations at the concentrations indicated throughout. Viable cells were counted for each sample taken as outlined below. Antibody titre for each sample taken was determined as outlined below.

Viable Cell Count

Culture was diluted as necessary in culture medium. It was examined microscopically in a haemocytometer (Neubauer counting chamber) using Erythrosin B (Sigma) 0.04% w/v in PBS, pH 7 as an exclusion dye. The number of viable and non-viable cells per milliliter and the percentage viability of the culture was calculated.

Antibody Titre

The quantity of Human IgG was determined by a Nephelometric method (Tanford, C. (1961) Light Scattering. Physical Chemistry of Macromolecules. New York:Wiley, 275–316; Whicher J. T et al (1978), "An evaulation of Hyland laser nephelometer PDQ system for the measurement of immunoglobulins"; Ann.Clin.Biochem. 15, p77–85), whereby the formation of insoluble immune-precipitin of Human IgG with highly specific antibody to Human IgG was measured. The Nephelometer measured the intensity of the light scattered by the insoluble immune-precipitin in reaction solution. The change in intensity of the scattered light signal is proportional to the concentration of Human IgG in tested sample. The quantity of Human IgG in the sample is measured from a standard curve constructed from known concentration of purified Human IgG versus the rate of light scatter signal.

Results

FIG. 1 illustrates a plot of antibody titre over time at various butyrate concentrations. Butyrate concentrations of 0.1 mM and 0.075 mM demonstrated a marked increase in antibody titre over control following 56 day culture. Butyrate concentrations of 0.1 mM demonstrated erratic protein production during the culturing process whereas at 0.075 mM a more consistent production was observed.

FIG. 2 illustrates a plot of antibody production by viable cell count over 56 day culture. Cells cultured in the presence of butyrate at 0.075 mM showed a slight decrease in viable cell count during the early stages of the culturing process which decrease had, by 56 day, narrowed considerably when compared to control. This may indicate that NS0 cells cultured in butyrate (0.075 mM) develop a degree of adaptation or tolerance to the presence of butyrate at around this concentration. Antibody titre at 0.075 mM showed a marked increase over control.

What is claimed is:

1. A process for the production of a protein by a cell in culture, comprising:
    (a) providing a eukaryotic cell that constitutively produces a protein, and
    (b) culturing said eukaryotic cell on a medium comprising an alkanoic acid component selected from the group consisting of:
        (i) alkanoic acids,
        (ii) salts of alkanoic acids, and
        (iii) a combination of alkanoic acids and salts of alkanoic acids, said alkanoic acid component maintained in the medium at a concentration of about 0.075 mM or less.

2. A process according to claim 1 comprising first culturing said eukaryotic cell on a cell culture medium that does not contain an alkanoic acid component, prior to culturing on a medium containing an alkanoic acid component.

3. A process according to claim 1, further comprising separating said protein from the culture medium.

4. A process according to claim 1 where said eukaryotic cell is cultured on said medium comprising an alkanoic acid component for at least ten days.

5. A process according to claim 1, further comprising subculturing the cell culture resulting from step (b), said subculture on medium comprising an alkanoic acid component selected from the group consisting of:
   (i) alkanoic acids,
   (ii) salts of alkanoic acids, and
   (iii) a combination of alkanoic acids and salts of alkanoic acids, said alkanoic acid component maintained in the subculture medium at a concentration of less than 0.075 mM.

6. A process according to claim 1 wherein said alkanoic acid component is a straight chain $C_{2-10}$.

7. A process according to claim 1 wherein said alkanoic acid component is a straight chain $C_{3-6}$.

8. A process according to claim 1 wherein the alkanoic acid component is selected from the group consisting of butyric acid and metal salts of butyric acid.

9. A process according to claim 1 wherein the alkanoic acid component is sodium butyrate.

10. A process according to claim 1 wherein the concentration of said alkanoic acid component is less than about 0.075 mM but greater than 0.025 mM.

11. A process according to claim 1, wherein said concentration of said alkanoic acid component is less than about 0.075 mM but greater than 0.05 mM.

12. A process according to claim 1, wherein said concentration of said alkanoic acid component is about 0.075 mM.

13. A process according to claim 1 wherein said eukaryotic cells are selected from non-immunoglobulin secreting mouse myeloma B cells (NSO) and Chinese Hamster Ovary (CHO) cells.

14. A process according to claim 1 wherein said protein is selected from the group consisting of hormones, enzymes, enzyme inhibitors, lymphokines, and immunoglobulins.

15. A process according to claim 1 wherein said protein is an immunoglobulin.

16. A process for the production of a protein by a cell in culture, comprising:
   (a) providing a eukaryotic cell that constitutively produces a protein, and
   (b) culturing said eukaryotic cell on a medium comprising an alkanoic acid component selected from the group consisting of:
      (i) butyric acid,
      (ii) metal salts of butyric acid, and
      (iii) a combination of butyric acid and a metal salt of butyric acid, said alkanoic acid component maintained in the medium at a concentration of about 0.075 mM or less.

17. A process according to claim 16 comprising first culturing said eukaryotic cell on a cell culture medium that does not contain an alkanoic acid component, prior to culturing on a medium containing an alkanoic acid component.

18. A process according to claim 16, further comprising separating said protein from the culture medium.

19. A process according to claim 16 where said eukaryotic cell is cultured on said medium comprising an alkanoic acid component for at least ten days.

20. A process according to claim 16 wherein the alkanoic acid component is sodium butyrate.

21. A process according to claim 16 wherein the concentration of said alkanoic acid component is less than about 0.075 mM but greater than 0.025 mM.

22. A process according to claim 16, wherein said concentration of said alkanoic acid component is less than about 0.075 mM but greater than 0.05 mM.

23. A process according to claim 16, wherein said concentration of said alkanoic acid component is about 0.075 mM.

24. A process according to claim 16 wherein said eukaryotic cells are selected from non-immunoglobulin secreting mouse myeloma B cells (NSO) and Chinese Hamster Ovary (CHO) cells.

25. A process according to claim 16 wherein said protein is selected from the group consisting of hormones, enzymes, enzyme inhibitors, lymphokines, and immunoglobulins.

26. A process according to claim 16 wherein said protein is an immunoglobulin.

* * * * *